(12) United States Patent
Kristoffersen et al.

(10) Patent No.: US 8,475,380 B2
(45) Date of Patent: Jul. 2, 2013

(54) REDUCTION OF MULTILINE ARTIFACTS IN DOPPLER IMAGING

(75) Inventors: Kjell Kristoffersen, Horton (NO); Hans Torp, Trondheim (NO); Tore Gruner Bjastad, Trondheim (NO); Lasse Lovstakken, Trondheim (NO); Torbjorn Hergum, Trondheim (NO); Johan Kirkhorn, Horten (NO)

(73) Assignee: General Electric Company, Schenectady, NY (US)

( * ) Notice: Subject to any disclaimer, the term of this patent is extended or adjusted under 35 U.S.C. 154(b) by 820 days.

(21) Appl. No.: 12/550,803

(22) Filed: Aug. 31, 2009

(65) Prior Publication Data

US 2011/0054316 A1   Mar. 3, 2011

(51) Int. Cl.
*A61B 8/00* (2006.01)
(52) U.S. Cl.
USPC ........... 600/443; 600/407; 600/437; 600/455; 600/457
(58) Field of Classification Search
USPC ............................ 600/437, 44, 455, 457, 443
See application file for complete search history.

(56) References Cited

U.S. PATENT DOCUMENTS

| | | | |
|---|---|---|---|
| 5,623,928 A | | 4/1997 | Wright et al. |
| 6,315,723 B1 * | | 11/2001 | Robinson et al. ............. 600/443 |
| 6,482,157 B2 | | 11/2002 | Robinson |
| 7,347,820 B2 * | | 3/2008 | Bonnefous .................... 600/437 |
| 2007/0055160 A1 * | | 3/2007 | Ng ................................ 600/447 |

FOREIGN PATENT DOCUMENTS

WO    2008068709    6/2008

OTHER PUBLICATIONS

Hergum, Torbjorn et al., "Parallel Beamforming Using Synthetic Transmit Beams," IEEE Transactions on Ultrasonics, Ferroelectrics, and Frequency Control, vol. 54, No. 2, Feb. 2007.

* cited by examiner

*Primary Examiner* — Unsu Jung
*Assistant Examiner* — Daniel Huntley
(74) *Attorney, Agent, or Firm* — McAndrews, Held & Malloy, Ltd.; David Bates; Jacob Groethe

(57) ABSTRACT

Certain embodiments of the present technology provide systems and methods that provide reduction of multiline artifacts in Doppler imaging. Certain embodiments provide for various ensembles of transmit beams at different spatial locations and overlapping receive beams between the locations. Certain embodiments provide for calculating various auto-correlation estimates based on the received beams and then combining the auto-correlation estimates to create an image. In certain embodiments, combining the auto-correlation estimates comprises applying a linear interpolation filter that decreases the weight applied for receive beams that are spatially located further away from the transmit beam.

24 Claims, 15 Drawing Sheets

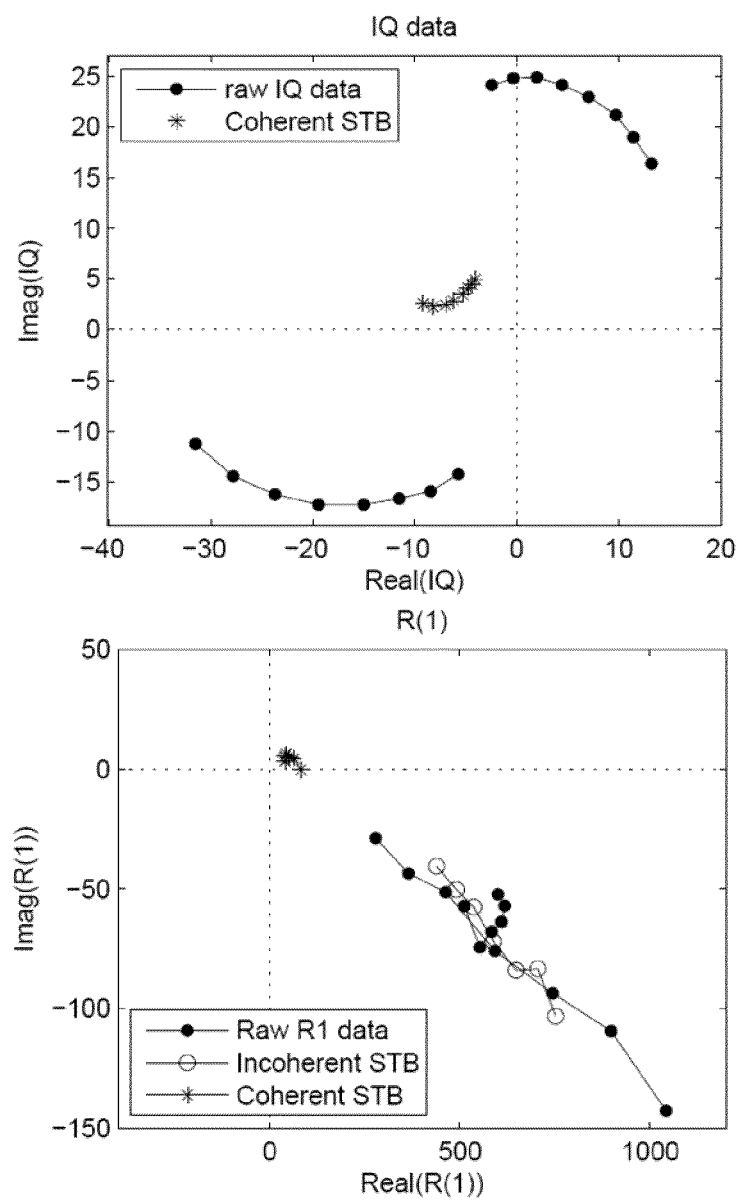

REDUCTION OF MULTILINE ARTIFACTS IN DOPPLER IMAGING

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Embodiments of the present technology generally relate to ultrasonic imaging. More particularly, embodiments of the present technology relate to reduction of multiline artifacts in Doppler imaging.

Doppler imaging uses reflected ultrasound waves to evaluate blood as it flows through a blood vessel. Doppler imaging can be used to evaluate blood flow through arteries and veins. Doppler imaging can indicate blocked or reduced blood flow through narrowed arteries, which can lead to a stroke. Doppler imaging can also reveal blood clots in veins that could break loose and block blood flow.

During Doppler imaging, a handheld instrument (transducer) is passed over the skin above a blood vessel. The transducer sends and receives ultrasound waves. The ultrasound waves bounce off solid objects, including blood cells. Movement of blood cells can cause a change in pitch of the reflected sound waves (called the Doppler effect). If there is no blood flow, the pitch does not change. Information from the reflected sound waves can be processed to provide graphs or pictures that represent the flow of blood through the blood vessels.

Types of Doppler imaging include, for example, continuous wave Doppler, duplex Doppler, color flow, power Doppler and B-flow. In color flow imaging, ultrasound signals are converted into colors that are overlaid on an image of a blood vessel, and the colors represent speed and direction of blood flow through the vessel.

Increasing the frame rate in ultrasonic imaging is desirable. Parallel receive beams can be used to increase the frame rate during multiline image acquisition. However, using parallel receive beams can introduce artifacts in images, for example, due to misalignment of transmit and receive beams. The trade-off between frame rate and image quality can lead to suboptimal images for medical diagnosis.

Needless to say, forming a best possible image for different anatomies and patient types is important to diagnostic imaging systems. Poor image quality may prevent reliable analysis of an image. For example, a decrease in image contrast quality may yield an unreliable image that is not usable clinically. Additionally, the advent of real-time imaging systems has increased the importance of generating clear, high quality images.

Techniques aimed at improving image quality during multiline image acquisition have been proposed, for example, in U.S. Pat. No. 6,482,157, issued to Robinson on Nov. 19, 2002, and the article "Parallel Beamforming Using Synthetic Transmit Beams," IEEE Transactions on Ultrasonics, Ferroelectrics, and Frequency Control, vol. 54, No. 2, February 2007. As discussed herein, it has been found that such proposed techniques are of limited effectiveness in connection with Doppler imaging.

A method and apparatus for multiline color flow and angio ultrasound imaging aimed at improving image quality is suggested in International Publication No. WO 2008/068709 A1, which names Clark and was published on Jun. 12, 2008. However, the International Publication does not disclose the techniques disclosed herein.

Thus, there is a need for improved systems and methods that can reduce multiline artifacts in Doppler imaging.

BRIEF SUMMARY OF THE INVENTION

Certain embodiments of the present technology provide systems, methods and computer-readable storage mediums encoded with sets of instructions for execution on a processing device and associated processing logic that provide for reduction of multiline artifacts in Doppler imaging.

In certain embodiments, for example, a method for multiline ultrasound imaging includes: transmitting a first ensemble of ultrasound beams at a first spatial position, wherein transmission of each beam in the first ensemble results in a plurality of parallel receive beams that are located between the first spatial position and a second spatial position; transmitting a second ensemble of ultrasound beams at the second spatial position, wherein transmission of each beam in the second ensemble results in a plurality of parallel receive beams that are located between the first spatial position and the second spatial position; calculating a first auto-correlation estimate based on at least two receive beams from said first ensemble of beams; calculating a second auto-correlation estimate based on at least two receive beams from said second ensemble of beams; combining the first auto-correlation estimate and the second auto-correlation estimate.

In certain embodiments, for example, an ultrasound imaging system includes: a transducer configured to transmit and receive ultrasound beams; and a control processor operably connected to the transducer, the control processor configured to process information received at the transducer, wherein the transducer is configured to transmit a first ensemble of ultrasound beams at a first spatial position, wherein transmission of each beam in the first ensemble results in a plurality of parallel receive beams that are located between the first spatial position and a second spatial position, wherein the transducer is configured to transmit a second ensemble of ultrasound beams at the second spatial position, wherein transmission of each beam in the second ensemble results in a plurality of parallel receive beams that are located between the first spatial position and the second spatial position, wherein the control processor is configured to a first auto-correlation estimate based on at least two receive beams from said first ensemble of beams, wherein the control processor is configured to calculate a second auto-correlation estimate based on at least two receive beams from said second ensemble of beams, and wherein the control processor is configured to combine the first auto-correlation estimate and the second auto-correlation estimate.

In certain embodiments, for example, a computer-readable storage medium encoded with a set of instructions for execution on a processing device and associated processing logic, includes: a first routine that provides for controlling a transducer configured to transmit and receive ultrasound beams; and a second routine that provides for calculation of a plurality of auto-correlation estimates and combination of the auto-correlation estimates, wherein the first routine provides for transmission of a first ensemble of ultrasound beams at a first spatial position, wherein transmission of each beam in the first ensemble results in a plurality of parallel receive beams that are located between the first spatial position and a second spatial position, wherein the first routine provides for transmission of a second ensemble of ultrasound beams at the second spatial position, wherein transmission of each beam in the second ensemble results in a plurality of parallel receive beams that are located between the first spatial position and the second spatial position, wherein the second routine provides for calculation of a first auto-correlation estimate based on at least two receive beams from said first ensemble of beams, wherein the second routine provides for calculation of a second auto-correlation estimate based on at least one receive beam in the second plurality of parallel receive beams and at least one receive beam in the fourth plurality of parallel receive beams, and wherein the second routine provides for combining the first auto-correlation estimate and the second auto-correlation estimate.

In certain embodiments, for example, the combined auto-correlation estimates are used to make an image. In certain embodiments, for example, each receive beam used to calculate the first auto-correlation estimate and the second auto-correlation estimate substantially overlap spatially. In certain embodiments, for example, each receive beam used to calculate the first auto-correlation estimate and the second auto-correlation estimate completely overlap spatially. In certain embodiments, for example, wherein half of the parallel receive beams that result from transmission of the first ensemble are located between the first spatial position and the second spatial position, and half of the parallel receive beams that result from transmission of the second ensemble are located between the first spatial position and the second spatial position. In certain embodiments, for example, all beams in the first ensemble are transmitted before any beams in the second ensemble are transmitted. In certain embodiments, for example, combining the first auto-correlation estimate and the second auto-correlation estimate comprises applying a linear interpolation function that decreases the weight applied for receive beams that are spatially located further away from the transmit beam.

BRIEF DESCRIPTION OF THE DRAWINGS

FIG. 7A (upper portion) illustrates a plot of raw RF/IQ data recorded from a beating heart and coherent STB interpolation of that data, and FIG. 7A (lower portion) illustrates a plot of auto-correlation estimates based on raw RF/IQ data, coherent STB interpolation of that data, and incoherent STB interpolation of that data.

Figure 1:
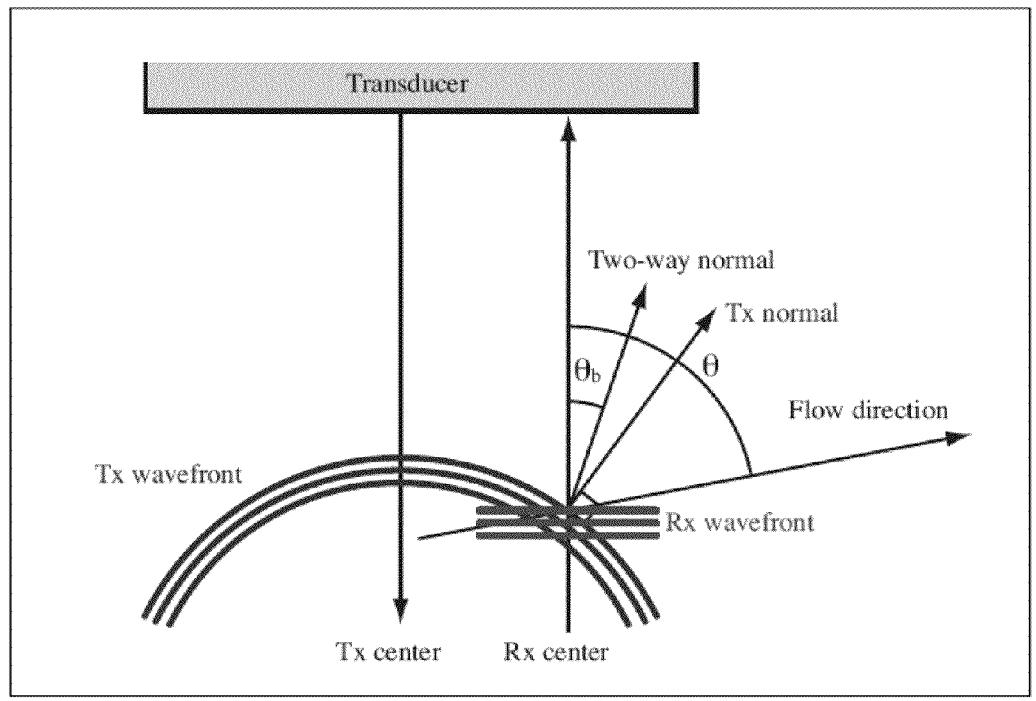
FIG. 1 illustrates a geometric model of a transmit wavefront emitted from a transducer and a receive wavefront.

The foregoing summary, as well as the following detailed description of embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EMBODIMENTS

Embodiments of the present technology generally relate to ultrasonic imaging. More particularly, embodiments of the present technology relate to reduction of multiline artifacts in Doppler imaging.

Types of Doppler imaging include, for example, continuous wave Doppler, duplex Doppler, color flow, power Doppler and B-flow.

Doppler imaging techniques may apply an auto-correlation function to create images from ultrasound signals. The auto-correlation function from an ultrasound signal $z(k)$ is $R(m) = \langle z(k+m)z(k)^* \rangle$, where m is the lag between a first signal and a second signal. The auto-correlation function can be estimated from a packet of N signals by applying the equation below.

$$R_N(m) = \frac{1}{N}\sum_{k=1}^{N} z(k+m)z(k)^*.$$

B-mode imaging (non-Doppler) does not apply the auto-correlation function above to create images from ultrasound signals. Techniques aimed at improving image quality during multiline image acquisition in connection with B-mode imaging have been proposed. However, it has been found that such proposed techniques are of limited effectiveness in connection with Doppler imaging.

In B-mode imaging, two causes of artifacts created during multiline image acquisition are skewing and warping. Skewing is the distortion of the two-way beam caused by misalignment of the transmit and receive beams. This misalignment also causes warping, where the receive-beam is pulled towards the center of the transmit beam, such that the received signals do not originate from the apparent direction of the receive-beam.

In addition to the parallel beamforming artifacts found in B-mode imaging, it has been found that a difference in curvature of transmit and receive beams gives a bias in the Doppler velocity estimates. The bias is dependent on the angle between the transmit and receive beams and the direction of the blood flow. For parallel beams, the curved wavefront of a focused transmit beam will cause a changing angle with the blood flow, depending on the position of the received beam. This causes a discontinuity in the velocity estimates between groups of beams from different transmit events. This bias can cause a discontinuity in the velocity estimates in Doppler images, resulting in artifacts.

FIG. 1 depicts a geometric model of a transmit wavefront (Tx wavefront) emitted from a transducer and a receive wavefront (Rx wavefront). The transmit wavefront is typically wide to fit all the parallel beams, and focused to increase the signal to noise ratio. Away from the focal point this makes the transmit wavefront wide and curved. The receive wavefront is typically dynamically focused and narrower than the transmit wavefront, so it will have a different curvature, or not be curved at all, and overlap with a small part of the transmit wavefront.

Also shown in FIG. 1 are the center of Tx wavefront (Tx center), the center of Rx wavefront (Rx center), the direction of blood flow (Flow direction), the direction perpendicular to Tx wavefront at Rx center (Tx normal), the vector sum of the Tx wavefront direction and the Rx wavefront direction (Two-way normal), the angle between Rx center and the flow direction ($\theta$), and the angle between Rx center and Two way normal ($\theta_b$). The geometric model of FIG. 1 is valid far from the focal point. In practice, the wavefronts in the focal point are planar, meaning that $\theta_b$ will approach zero when the diffracting effects overcome the geometric focusing effect. FIG. 1 provides an example where curved wave fronts above the focal point cause a varying angle between the flow and the receive-beams, depending on how far the receive-beam is steered off the axis of the transmitted beam. This is seen in Doppler images as abrupt changes in velocity estimates from one group of received beams to the next.

When the curvature is not taken into account the expected Doppler shift ($f_d$) is represented by the equation:

$$f_d = \frac{2vf_0}{c} \cos(\theta),$$

where v is the velocity of the blood, $f_0$ is the transmit frequency, c the speed of sound, and $\theta$ the angle between the receive beam center and the direction of the blood flow (as depicted in FIG. 1).

The actual Doppler shift will be biased due to $\theta_b$ (the angle between the receive center and the two way normal, as depicted in FIG. 1), providing the biased Doppler shift ($f_b$), which is represented by the equation:

$$f_b = \frac{2vf_0}{c} \cos(\theta - \theta_b).$$

The relative difference between the expected and the measured Doppler shift is represented by the equation:

$$\frac{f_b - f_d}{f_d} = \frac{\cos(\theta - \theta_b) - \cos(\theta)}{\cos(\theta)}.$$

Figure 2:
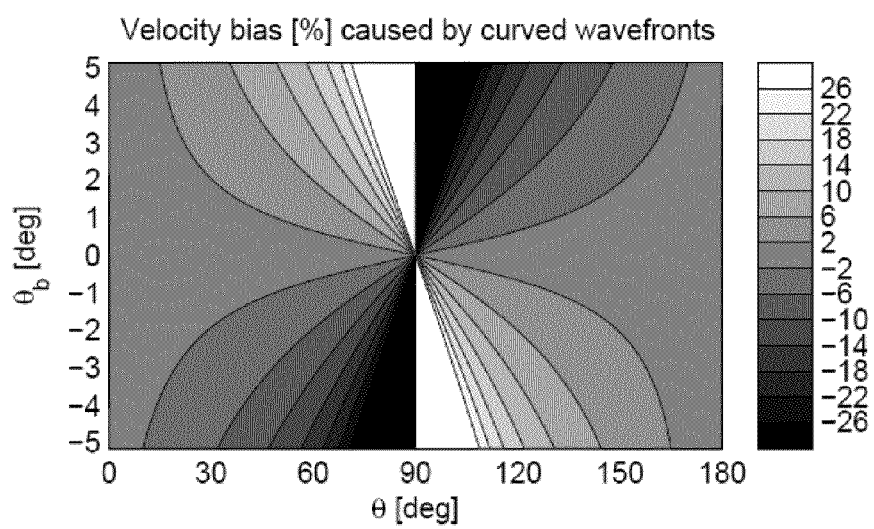
FIG. 2 illustrates a diagram the percent velocity bias (Doppler bias) caused by curved wavefronts.

This relationship is plotted in FIG. 2, which depicts the percent velocity bias (Doppler bias) caused by curved wavefronts for relevant combinations of angles $\theta$ and $\theta_b$. FIG. 2 depicts ±30% Doppler bias to avoid showing the asymtote near $\cos(\theta)=0$. Based on FIG. 2, it can be expected that the Doppler bias will be most visible when the angle between the Two way normal and the Flow direction (as depicted in FIG. 1) is large.

Figure 3:
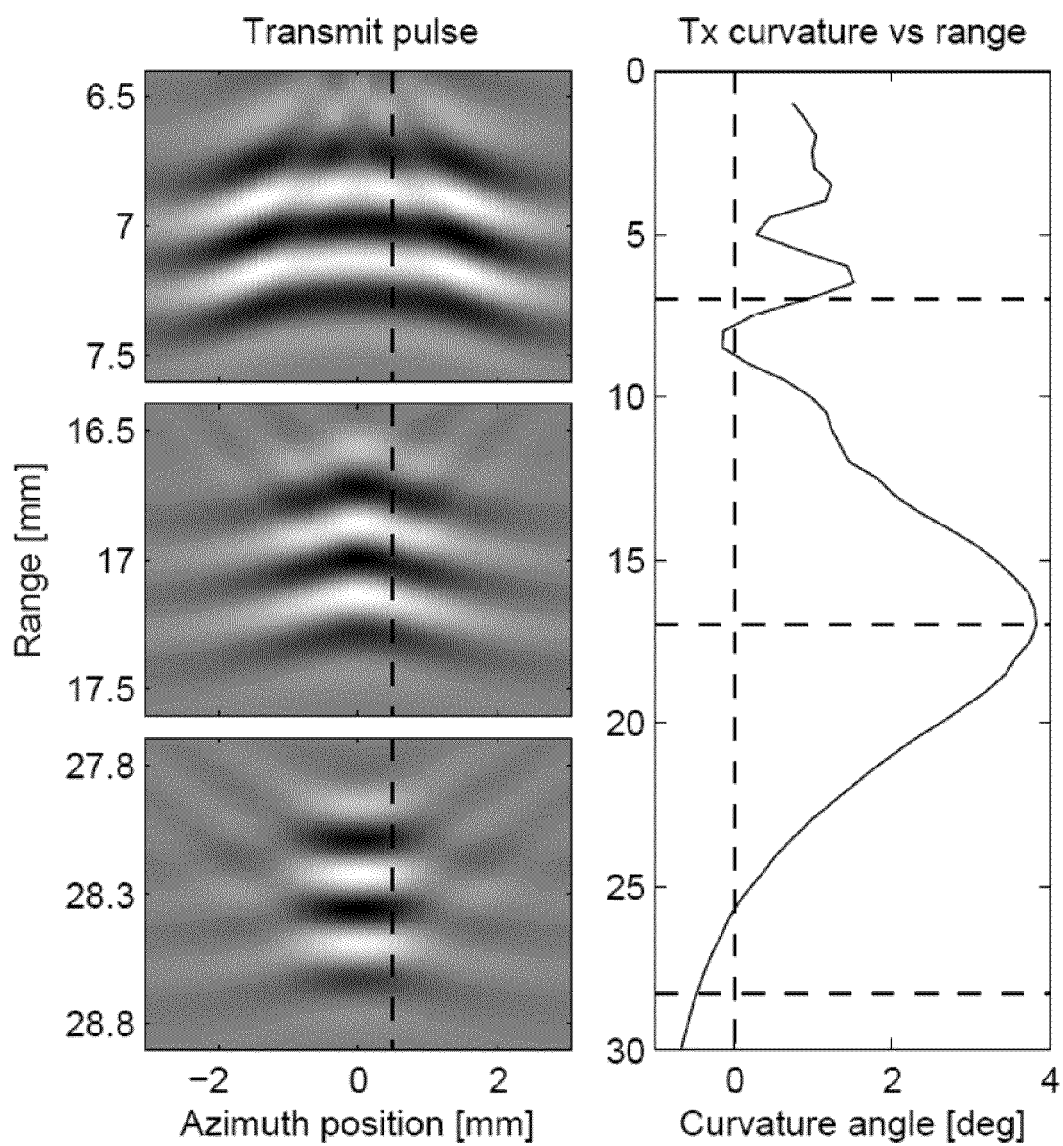
FIG. 3 illustrates computer simulation results that characterize the depth-dependence of beam curvature.

FIG. 3 depicts computer simulation results that characterize the depth-dependence of beam curvature by showing the transmit pulse as a function of range and azimuth position, and estimated curvature (based on the phase variation laterally across the simulated transmit pulse at each depth). The left portion of FIG. 3 depicts a transmitted pulse at three depths: in the nearfield (range=6.5 to 7.5 mm), at the position of peak curvature (range=16.5 to 17.5 mm), and at the focal point (range=27.8 to 28.8 mm). The vertical dashed line indicates the position of the most steered receive beam. The right portion of FIG. 3 provides the estimated curvature along the vertical dashed line. The horizontal dashed lines in the right portion of FIG. 3 indicate the positions of the three pulse depths shown in the left portion of FIG. 3. The simulation parameters correspond to the carotid in vivo parameters discussed herein in connection with Table I.

Figure 4:
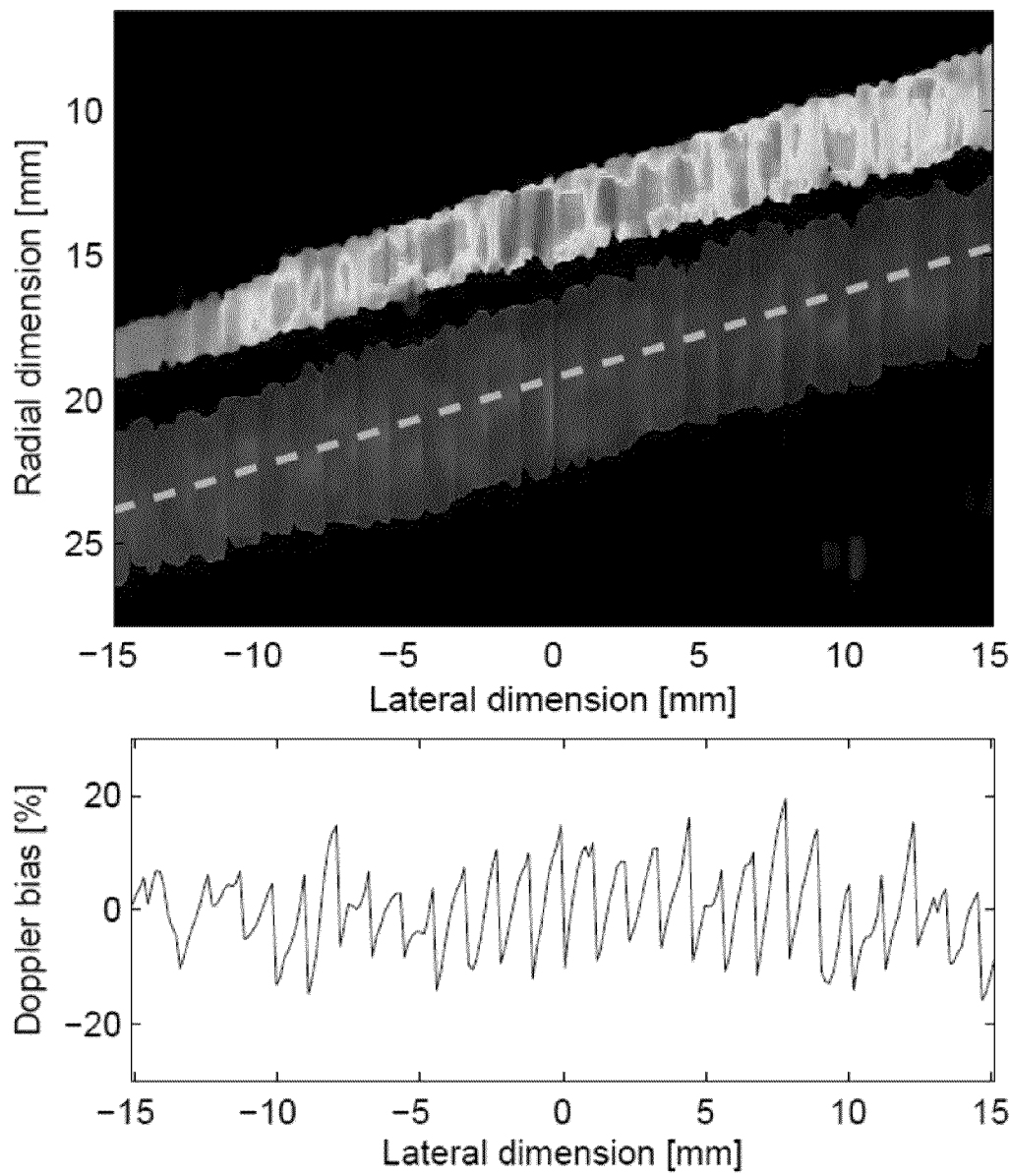
FIG. 4 (upper portion) illustrates an in vivo example of the carotid artery without any lateral smoothing, and FIG. 4 (lower portion) illustrates a plot of the deviation from the average velocity along the center of the carotid artery (along the dashed line in the upper portion of FIG. 4).

Because the Doppler bias is symmetric about the center of the transmit beam, but with opposite signs, it will cause the velocity estimates to change abruptly between two neighboring beams from different transmit events. This is shown in FIG. 4, which depicts (in the upper portion) an in vivo example of the carotid artery without any lateral smoothing. Note the vertical discontinuities of the velocity estimates, which appear at the transitions between beams from different transmit events. The vertical discontinuities from transition between groups of parallel beams are visible, particularly in the regions with velocity aliasing. This is also shown in the bottom portion of FIG. 4, where the deviation from the average velocity along the center of the carotid artery (along the dashed line in the upper portion of FIG. 4) is plotted (Doppler bias in % vs. lateral dimension in mm). Ideally this should be a smooth curve near zero.

Thus, in addition to the parallel beamforming artifacts found in B-mode imaging, it has been found that a difference in curvature of transmit and receive beams gives a bias in the Doppler velocity estimates. This is one of the reasons that proposed techniques aimed at improving image quality during multiline image acquisition in connection with B-mode (non-Doppler) imaging are of limited effectiveness in connection with Doppler imaging.

Methods of using synthetic transmit beams have previously been proposed to reduce artifacts created during multiline image acquisition in connection with B-mode imaging. For example, synthetic transmit beams have been used to reduce artifacts from parallel beams in B-mode imaging by interpolating between receive beams from different transmit events. As discussed in more detail below, this interpolation is done on the demodulated radiofrequency data acquired during image acquisition, also known as RF/IQ data. Known B-mode methods also do not provide for overlapping receive beams from sequential transmit events.

It has been found that combining overlapping receive beams from subsequent transmit events can provide advantages. However, for an interpolation based on RF/IQ data to work, the overlapping receive beams must sum coherently. For this reason, we will refer to the inventive process of interpolating between RF/IQ data of overlapping receive beams from different transmit events in order to reduce multiline artifacts in Doppler imaging as coherent STB.

Figure 5:
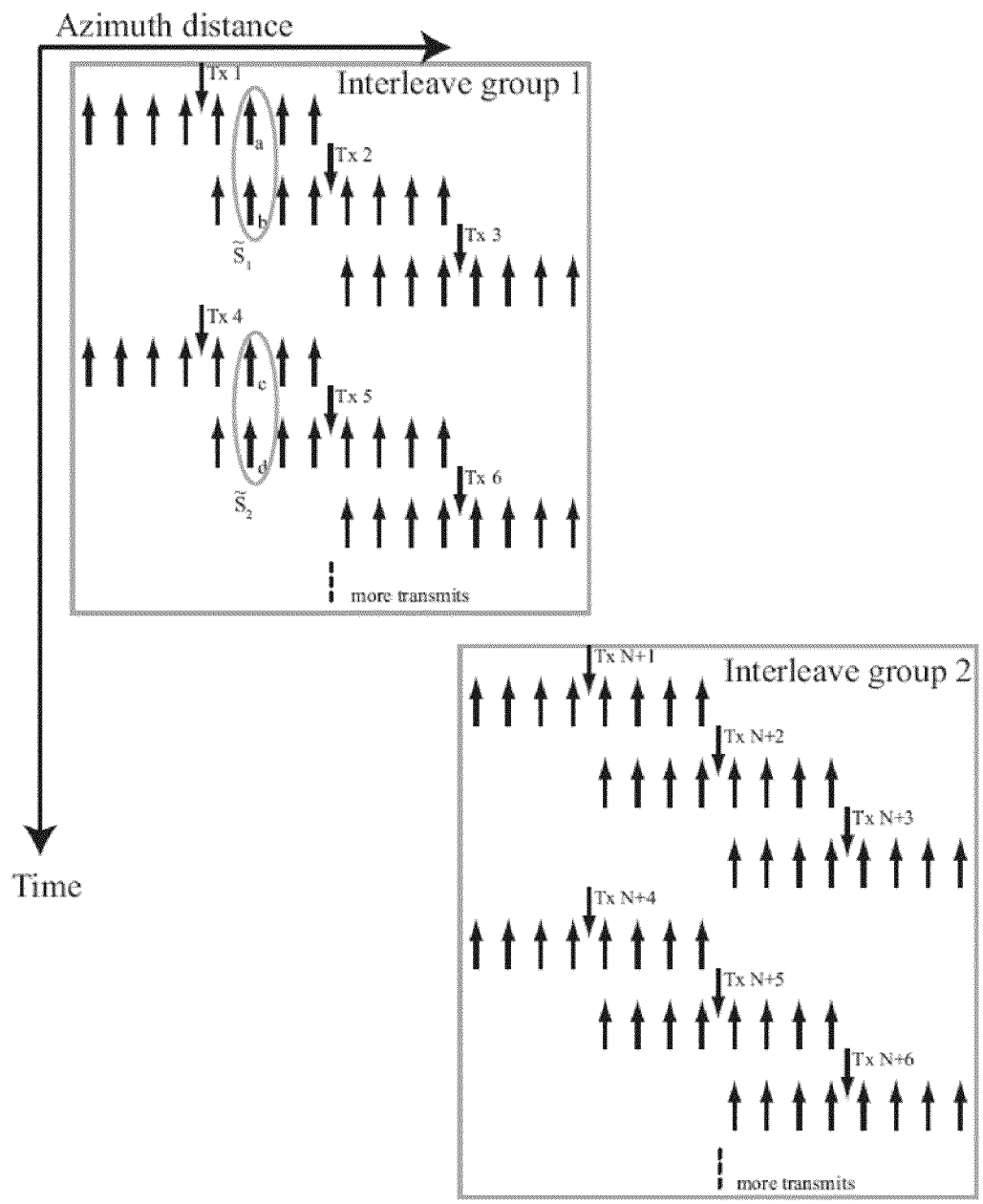
FIG. 5 illustrates transmit and receive beams as a function of azimuth distance and time in accordance with an embodiment of the present technology.

FIG. 5 depicts transmit and receive beams as a function of azimuth distance and time. Interleave group 1 depicts six transmissions, Tx 1, Tx 2, Tx 3, Tx 4, Tx 5 and Tx 6 and indicates that more transmits may be included. Interleave group 1 shows three ensembles of ultrasound beams transmitted at three spatial positions. A first ensemble of ultrasound beams including Tx 1 and Tx 4 are transmitted at the same spatial position. A second ensemble of ultrasound beams including Tx 2 and Tx 5 are transmitted at the same spatial position. Also, a third ensemble of ultrasound beams including Tx 3 and Tx 6 are transmitted at the same spatial position. Each transmission results in eight receive beams. The receive beams for subsequent transmissions are overlapping and the beam interleaving group size is 3. Interleave group 2 is similarly configured and includes transmit beams Tx N+1, Tx N+2, Tx N+3, Tx N+4, Tx N+5 and Tx N+6. Beam interleaving techniques can be used when acquiring overlapping beams.

The receive beams for subsequent transmissions overlap such that all of the receive beams (up-arrows) from Tx 1 that are positioned to the right of Tx 1 overlap with all of the receive beams (up-arrows) from Tx 2 that are positioned to the left of Tx 2. Likewise, all of the receive beams (up-arrows) from Tx 2 that are positioned to the right of Tx 2 overlap with all of the receive beams (up-arrows) from Tx 3 that are positioned to the left of Tx 3.

Synthetic transmit beam processing is done by interpolating between RF/IQ data of overlapping receive beams to give the signal, $\tilde{S}(x_r)$ represented by the following equation.

$$\tilde{S}(x_r) = \sum_k h(x_r, k) S_k(x_r),$$

where $h(x_r, k)$ is an interpolation filter and $S_k(x_r)$ is the signal received from transmitting towards direction k and receiving from direction r. A linear interpolation filter can be used to illustrate the principle, which only requires two overlapping receive beams to increase the frame rate. The interpolation filter has weights w and (1−w) where w is inversely proportional to the distance from the transmit beam, and can be defined by the equation:

$$w = \frac{x_r - x_k}{x_{k+1} - x_k}.$$

As an example, a signal $\tilde{S}_1$ can be made from the pair of beams a and b, as indicated in FIG. 5. As with B-mode images, this limits the artifacts caused by warping and skewing. Several such signals can be interpolated to estimate an auto-correlation function to be used in Doppler imaging. The cross correlation between two such synthetic transmit beam processed signals, $\tilde{S}_1$ and $\tilde{S}_2$, is represented by the following equations.

$$\tilde{S}_1 = \omega S_a + (1-\omega) S_b$$

$$\tilde{S}_2 = \omega S_c + (1-\omega) S_d$$

$$\langle \tilde{S}_1 \tilde{S}_2^* \rangle = \omega^2 \langle S_a S_c^* \rangle + \omega(1-\omega)\langle S_a S_d^* \rangle$$
$$(1-\omega)\omega\langle S_b S_c^* \rangle + (1-\omega)^2 \langle S_b S_d^* \rangle,$$

where the beams a, b, c and d are all received from the same direction, but from different transmit events as indicated in FIG. 5.

As discussed above, synthetic transmit beam processing can be done by interpolating between RF/IQ data of overlapping receive beams. In other words, a pair of overlapping receive beams can be used to create a signal (S). These signals (S) can be interpolated and then used to estimate an auto-correlation function to be used in Doppler imaging.

Again, this process of interpolating between RF/IQ data of overlapping receive beams from different transmit events in order to reduce multiline artifacts in Doppler imaging is herein referred to as coherent STB.

The received Doppler signal stays correlated only for a brief period of time, depending on the transit time of scatterers passing through the sample volume. When the acquisition time between two overlapping beams used to estimate the auto-correlation function is long, too many of the scatterers inside the sample volume are replaced, and the estimate can not reconstruct the auto-correlation function. This can happen for instance across interleave groups, as when the receive beams from Tx 3 are combined with receive beams from Tx N+1 in FIG. 5.

Figure 6:
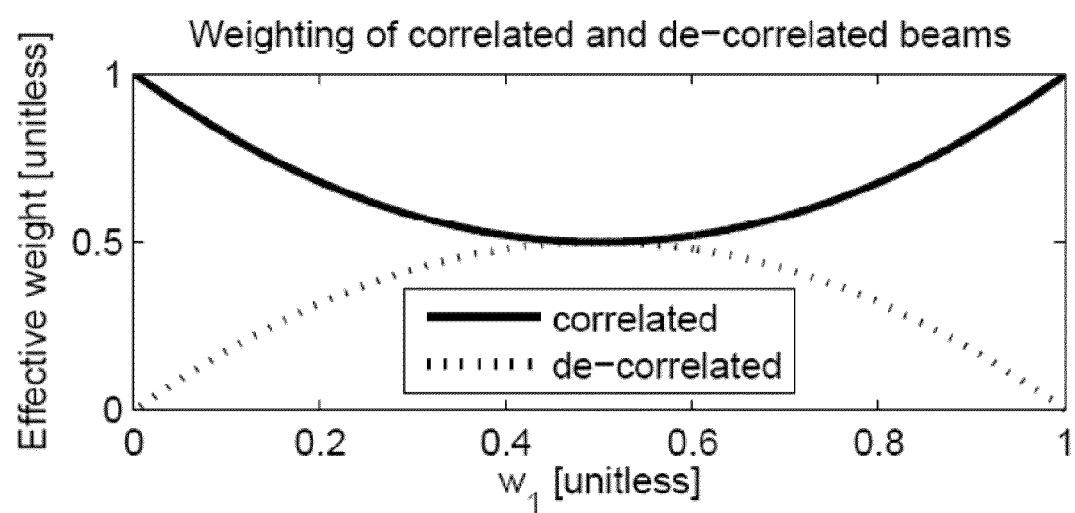
FIG. 6 illustrates a plot of the weighting of two correlated terms versus two un-correlated terms.

In such situations the two cross-terms in the middle of the equation:

$$\langle \tilde{S}_1 \tilde{S}_2^* \rangle = \omega^2 \langle S_a S_c^* \rangle + \omega(1-\omega)\langle S_a S_d^* \rangle$$
$$+(1-\omega)\omega\langle S_b S_c^* \rangle + (1-\omega)^2 \langle S_b S_d^* \rangle,$$

include terms with zero expected correlation, meaning they will only contribute with white noise. The weighting of the two correlated terms versus the two un-correlated terms changes depending on the distance from the position of the transmit beam. FIG. 6 plots these weights, $w^2+(1-w)^2$ versus $2w(1-w)$, and indicates that the de-correlated terms contribute more with increasing distance to the transmit beams. This means that in the case of a significant time lag between samples, the reconstruction will be best near the transmit beams and worst in the middle between them, reducing the spatial shift invariance of the imaging system.

It has also been found that the increased time difference between neighboring beams (increased lag) in Doppler acquisition can cause phase cancellation and therefore a failed reconstruction of synthetic transmit beams when using coherent STB. Constructive interference happens when the displacement between received pulses is less than or equal to $\lambda/8$, that is, when $\upsilon\tau=\Delta r \leq \lambda/8 = c/(8 f_0)$, where $\tau$ is the time lag between acquisition of the overlapping pulses, c is the speed of sound, and $f_0$ is the transmit frequency. In comparison the Nyquist sampling velocity for Doppler imaging is $\upsilon_n=c/2 f_0 \Delta t$ where $\Delta t$ is the time between pulses.

When the displacement between received pulses is greater than $\lambda/8$, the interpolation of RF/IQ data can give arbitrary results, for example, as is illustrated in the top portion of FIG. 7A, which plots raw RF/IQ data recorded from a beating heart and coherent STB interpolation of that data. Due to a large time delay between the combined samples, the samples are summed with nearly opposite phase, resulting in an arbitrary result. The bottom portion of FIG. 7 depicts auto-correlation estimates based on the interpolated RF/IQ data using coherent STB. Velocity estimates based on the raw RF/IQ data (without applying coherent STB) are also plotted. The results for the coherent STB plot are quite different than the results for the raw RF/IQ data.

The Doppler bias varies from beam to beam in a non-linear manner, as indicated in FIG. 2. This means that the Doppler bias cannot be removed entirely by coherent STB using linear interpolation. Nonetheless, as the bottom part of FIG. 4 indicates, the Doppler bias of the interpolated beams have opposite signs so the bias will be reduced by applying coherent STB and a linear interpolation filter.

In certain embodiments, other types of interpolation filters, such as a flat weighting filter or a higher order interpolation filter, for example, can be used instead of the linear interpolation filter. In certain embodiments, using a higher order interpolation filter can enable more of the non-linearly varying bias to be corrected for. However, to achieve this, more overlapping receive beams need to be combined, which increases the possibility of destructive interference happening from larger time differences between the samples. The number of overlapping beams equals the order of the interpolation filter (two for linear interpolation).

It has been found that interpolation of auto-correlation estimates obtained from overlapping receive beams, rather than interpolation between RF/IQ data of overlapping receive beams (as provided in connection with coherent STB), can provide reduction of multiline artifacts in Doppler imaging. This technique will be referred to herein as incoherent STB.

The bottom portion of FIG. 7A also depicts interpolation of auto-correlation estimates obtained from overlapping receive beams using incoherent STB. When compared to the velocity estimates based on the raw RF/IQ data, the results are similar, which indicates that the application of incoherent STB has provided a better representation of the raw RF/IQ data than the coherent STB application (and also allowed the reduction of artifacts from multiline acquisition). This is because the auto-correlation function, which is based on phase change between successive samples, is interpolated using incoherent STB, rather than the RF/IQ data, which is based on absolute phase information, being interpolated using coherent STB.

As discussed above, Doppler imaging techniques may apply an auto-correlation function to create images from ultrasound signals. The auto-correlation function from an ultrasound signal $z(k)$ is $R(m) = \langle z(k+m) z(k)^* \rangle$, where m is the lag between a first signal and a second signal. The auto-correlation function can be estimated from a packet of N signals by applying the equation below.

$$R_N(m) = \frac{1}{N} \sum_{k=1}^{N} z(k+m) z(k)^*.$$

Because the auto-correlation function varies relatively slowly (when compared to the rate at which the signal from blood de-correlates), by applying incoherent STB, image quality can be improved despite fast blood flow and/or despite acquisition of beams with an increased time difference between the beams (increased lag), for instance across interleaving groups or across scan planes in a 3D scan. This can provide improved image quality at increased frame rates during multiline image acquisition in connection with Doppler imaging.

It has been found that performing interpolation on the auto-correlation estimates using incoherent STB (instead of interpolating RF/IQ data using coherent STB) eliminates the cross-terms discussed above (in connection with coherent STB). This has been found to be desirable because the cross-terms contribute white noise when the time delay between subsequent transmissions is too long.

Figure 7B:
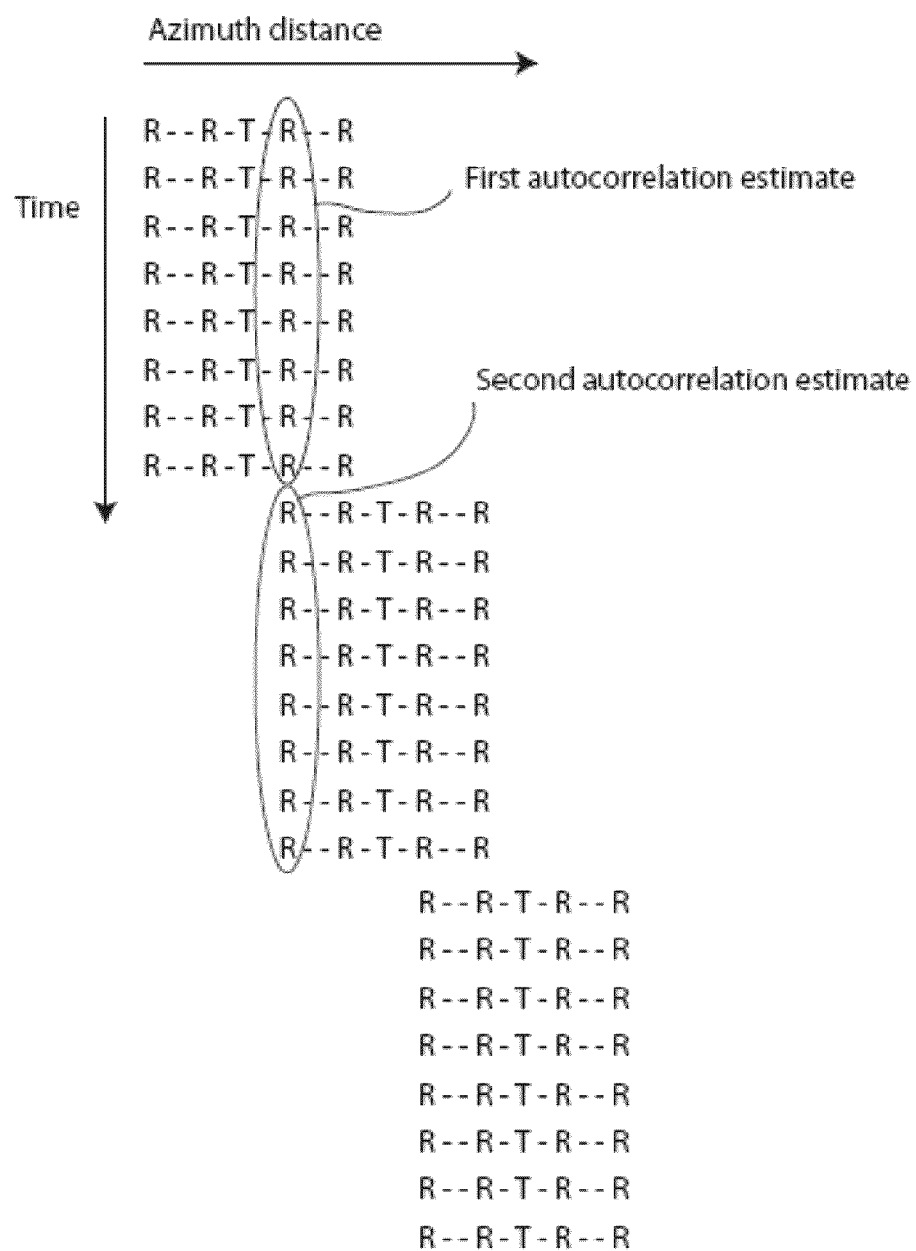
FIG. 7B illustrates transmit and receive beams as a function of azimuth distance and time in accordance with an embodiment of the present technology.

FIG. 7B depicts transmit and receive beams as a function of azimuth distance and time. At a first azimuth position, eight transmissions (T) are made one after the other (the eight transmissions at this position are a first ensemble of beams), each resulting in four parallel receive beams (R). Then, at a second azimuth position, eight transmissions (T) are made one after the other (the eight transmissions at this position are a second ensemble of beams), each resulting in four parallel receive beams (R). Then, at a third azimuth position, eight transmissions (T) are made one after the other (the eight transmissions at this position are a third ensemble of beams), each resulting in four parallel receive beams (R). Half of the receive beams from the first set of transmissions (at the first position) are located between the first position and the second position, and half of the receive beams from the second set of transmissions (at the second position) are located between the first position and the second position. As shown, some of the receive beams are overlapping such that they are at the same spatial position. Similarly, half of the receive beams from the second set of transmissions (at the second position) are located between the second position and the third position, and half of the receive beams from the third set of transmissions (at the third position) are located between the second position and the third position. Again, some of the receive beams are overlapping such that they are at the same spatial position.

Figure 7C:
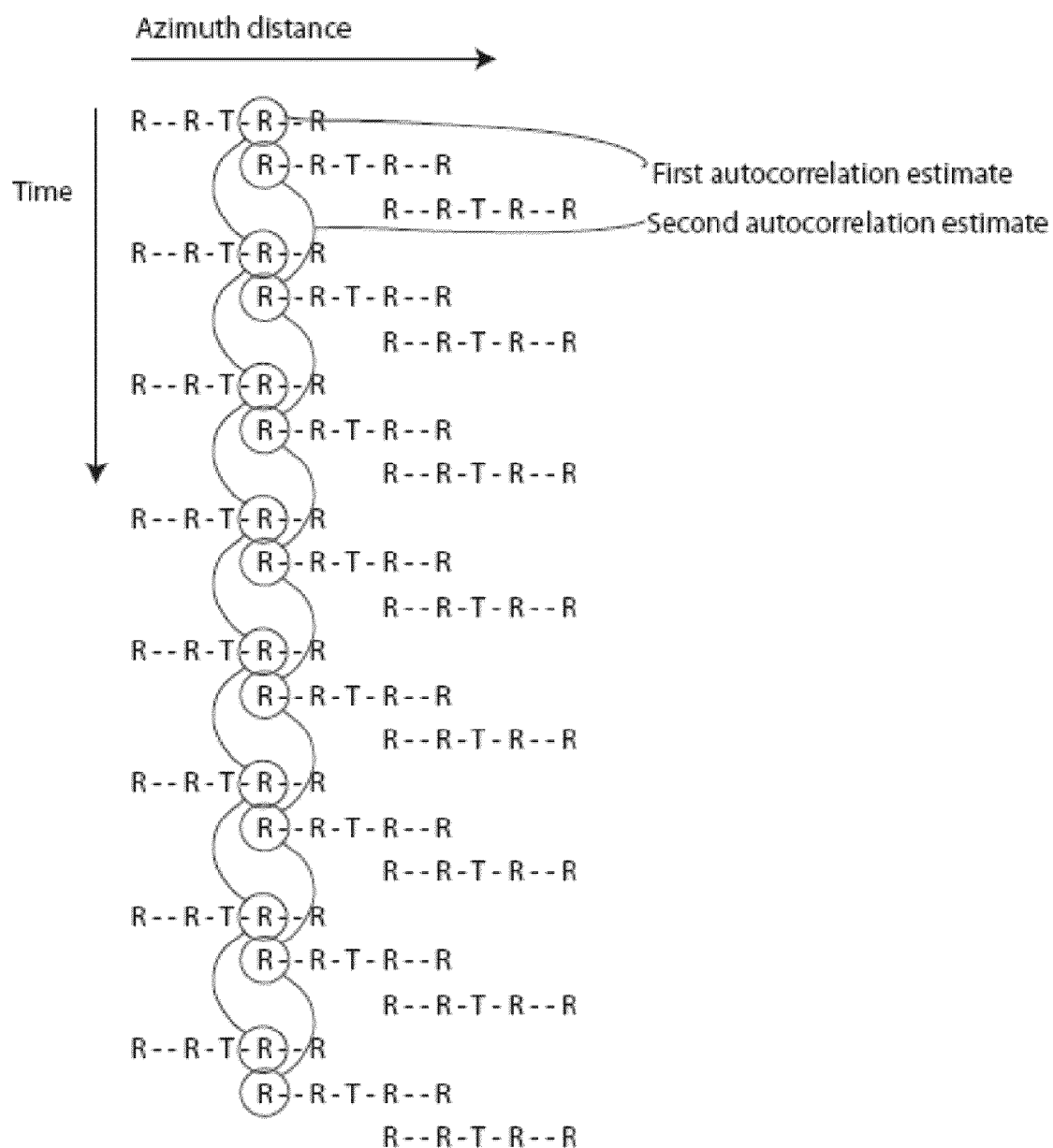
FIG. 7C illustrates transmit and receive beams as a function of azimuth distance and time in accordance with an embodiment of the present technology.

FIG. 7C depicts transmit and receive beams as a function of azimuth distance and time. FIG. 7C depicts one interleave group, with three transmit positions (T) resulting in four parallel receive beams (R) for each transmit. The first three transmit beams are spaced apart about the azimuth direction such that the first transmit beam is in a first position, the second transmit beam is in a second position, and the third transmit beam is in a third position. The eight transmit beams in the first spatial position are a first ensemble of beams. The eight transmit beams in the second spatial position are a second ensemble of beams. The eight transmit beams in the third spatial position are a third ensemble of beams. Half of the receive beams from the first transmit beam are located between the first position and the second position, and half of the receive beams from the second transmit beam are also located between the first position and the second position. As shown, some of the receive beams are overlapping such that they are at the same spatial position. Similarly, half of the receive beams from the second transmit beam are located between the second position and the third position, and half of the receive beams from the third transmit beam are also located between the second position and the third position. Again, some of the receive beams are overlapping such that they are at the same spatial position.

As shown in FIGS. 7B and 7C, a first auto-correlation estimate can be calculated based on receive beams at the same azimuth position that resulted from the eight transmissions at the first position. Similarly, a second auto-correlation estimate can be calculated based on receive beams at the same azimuth position that resulted from the eight transmissions at the second position. In certain embodiments, each receive beam used to calculate the first auto-correlation estimate and the second auto-correlation estimate substantially overlap spatially. In certain embodiments, each receive beam used to calculate the first auto-correlation estimate and the second auto-correlation estimate completely overlap spatially.

A synthetic auto-correlation estimate $\tilde{R}$ can be found by interpolating between the first auto-correlation estimate and the second auto-correlation estimate. The synthetic auto-correlation estimate $\tilde{R}$ can be calculated using the equation below.

$$\tilde{R}(x_i) = \sum_k h(x_i, k) R(k) = wR_1 + (1-w)R_2,$$

where $h(x_i, k)$ is a linear interpolation filter and $R(k)$ is the auto-correlation estimate at direction k. The interpolation filter has weights w and (1−w) where w is inversely proportional to the distance from the transmit beam, and can be defined by the equation:

$$w = \frac{x_r - x_k}{x_{k+1} - x_k}.$$

Again, this process of interpolating between auto-correlation estimates of overlapping receive beams from different transmit events in order to reduce multiline artifacts in Doppler imaging is herein referred to as incoherent STB.

As discussed above, it has been found that incoherent STB is more spatially shift invariant than coherent STB. This is because incoherent STB does not depend on absolute phase information (as coherent STB does), resulting in no lateral variation caused by combinations of signals acquired at significantly different time points, which can occur when using coherent STB. Some lateral variation due to the different signal to noise ratio of the acquired data will remain, however, this is inherent to all parallel beam processing methods when more than two parallel beams are considered.

Testing was conducted comparing coherent STB images, incoherent STB images and standard parallel beam images. In vivo color flow images were acquired using linear array imaging and phased array imaging. Image acquisition parameters for the in vivo color flow images created using linear array imaging and phased array imaging are provided in Table I.

TABLE I

SETTINGS FOR in vivo IMAGES.

| | Value |
| --- | --- |
| Linear array parameters | |
| Center frequency $f_O$ | 5.9 MHz |
| Tx f-number | 5 |
| Rx f-number | dynamic. min. 1.4 |
| Tx focal depth | 2.8 cm |
| Pulse length | 2.5 cycles |
| Packet size | 12 |
| Parallel beams acquired | 16 |
| Parallel beams synthesized | 8 |
| Pulse repetition frequency | 2000 |
| Lateral smoothing | none |
| Radial smoothing (R0) | none |
| Radial smoothing (R1) | 1.1 mm |
| Phased array parameters | |
| Center frequency $f_O$ | 2.5 MHz |
| Tx f-number | 18 |
| Rx f-number | dynamic. min. 1.5 |
| Tx focal depth | 14 cm |
| Pulse length | 2.5 cycles |

TABLE I-continued

SETTINGS FOR in vivo IMAGES.

| | Value |
| --- | --- |
| Packet size | 8 |
| Parallel beams acquired | 16 |
| Parallel beams synthesized | 8 |
| Pulse repetition frequency | 4000 |
| Radial smoothing | 1.5 mm |
| Lateral smoothing | none |

In connection with the linear array imaging, two sets of ultrasound images were acquired using a GE Vingmed E9 ultrasound scanner. One set of images that depict the common carotid artery and the internal jugular vein, were acquired using interleaving to maximize frame rate and maintain the desired Nyquist velocity. A second set of images were acquired, wherein the scan depth and desired Nyquist velocity were such that no beam interleaving could be applied. For both cases the same raw RF/IQ data was processed to get both coherent STB images, incoherent STB images and standard parallel beam images. In other words, all differences are due to post-processing and not differences in acquisition.

Figure 8:
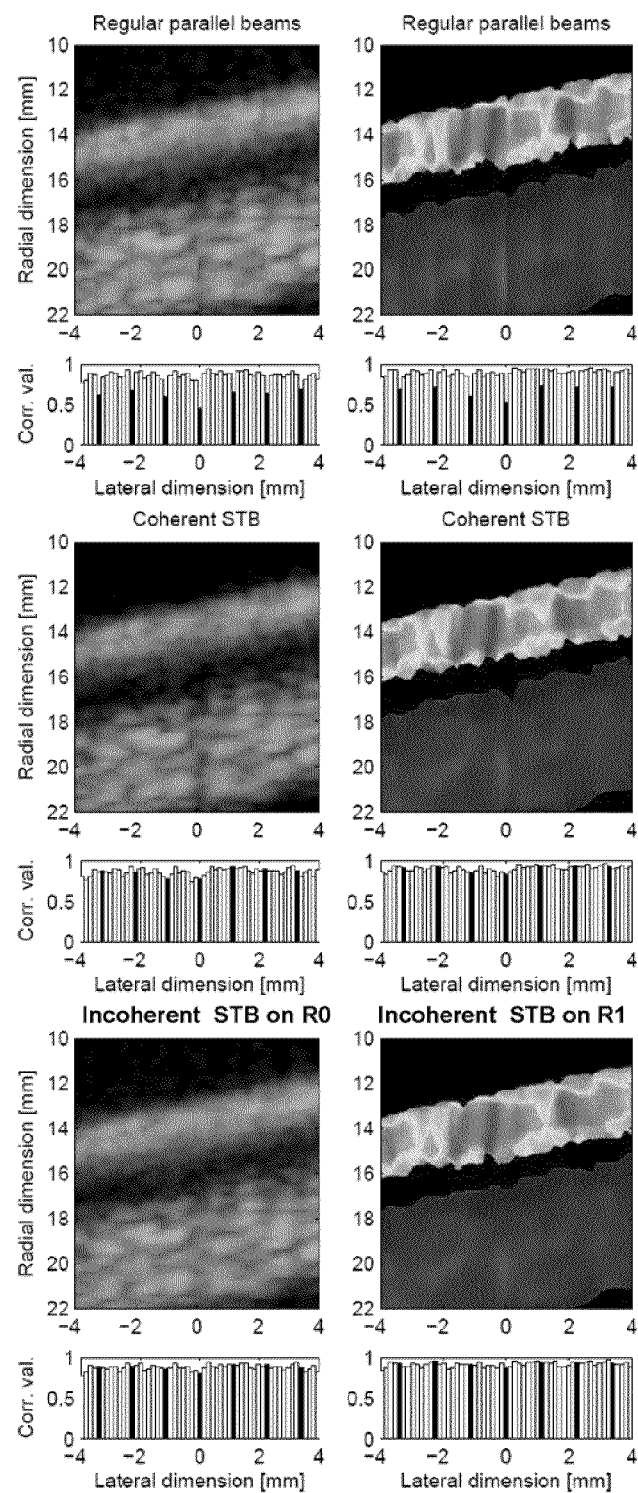
FIG. 8 illustrates power and velocity estimates of in vivo color flow images created using linear array imaging in accordance with embodiments of the present technology.

FIG. 8 depicts power and velocity estimates of in vivo color flow images created using linear array imaging. The top pane shows standard parallel beam processing, the middle pane shows coherent STB, and the bottom pane shows incoherent STB. The images on the left side of FIG. 8 depict power estimates and the images on the right side of FIG. 8 depict velocity estimates. Cross correlation between neighboring beams has previously been shown to be a good measure of parallel beam artifacts, so the cross correlation between the R(0) estimates of neighboring beams is shown beneath the power images, and the cross correlation between R(1) estimates are shown beneath the velocity images. To make the correlation estimates less noisy the cross correlation plots are made from the raw data of the whole cine loop, which consists of 44 frames. Note the differences in parallel beam artifacts, and the differences in beam-to-beam correlation between groups of parallel beams. There are four interleave groups, with transitions at [−7, 0, 7] mm, but only two interleave groups are shown in the cropped images.

Figure 9:
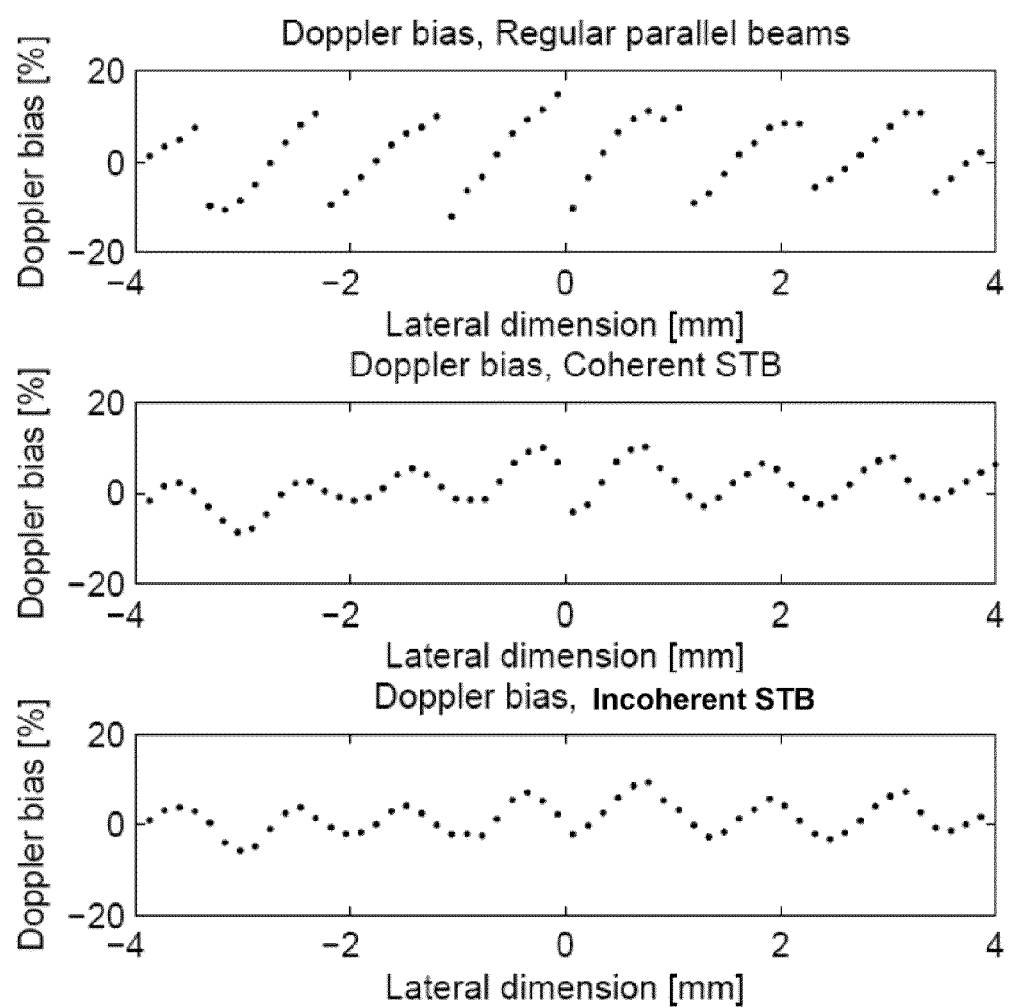
FIG. 9 illustrates Doppler bias based on the information depicted in FIG. 8.

The Doppler bias for the frame shown in FIG. 8 is shown in FIG. 9, which depicts the Doppler bias extracted from the center of the artery. Each dot represents the bias from one beam at the center of the artery. Notice the discontinuities in the bias at the transition between beams from different transmit events when regular parallel beams are used, and compare this to the two other approaches.

Figure 10:
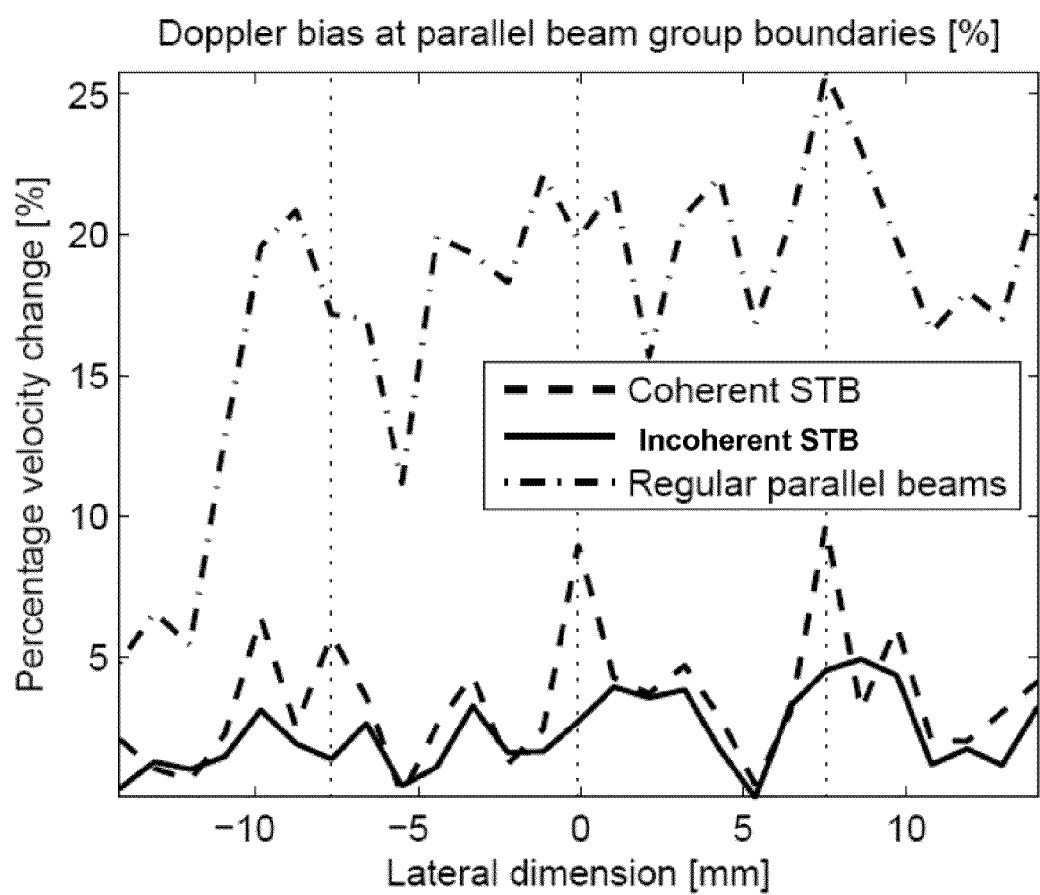
FIG. 10 illustrates Doppler bias at parallel beam group boundaries based on the information depicted in FIG. 8.

The relative change in velocity at these discontinuities are shown in FIG. 10, which depicts the Doppler bias across neighboring parallel beam groups. With constant flow and otherwise ideal conditions the values should be zero. The dashed vertical lines indicate the transition between interleaving groups. The source data for these plots are extracted from the center of the carotid artery and averaged over 7 frames. For the beams where the center of the artery is between 15 and 19 mm regular parallel beams had a mean bias and standard deviation of 19.9±3.0%, coherent STB showed a deviation of 3.8±2.3% and incoherent STB had the lowest deviation at 2.9±1.5%.

Figure 11:
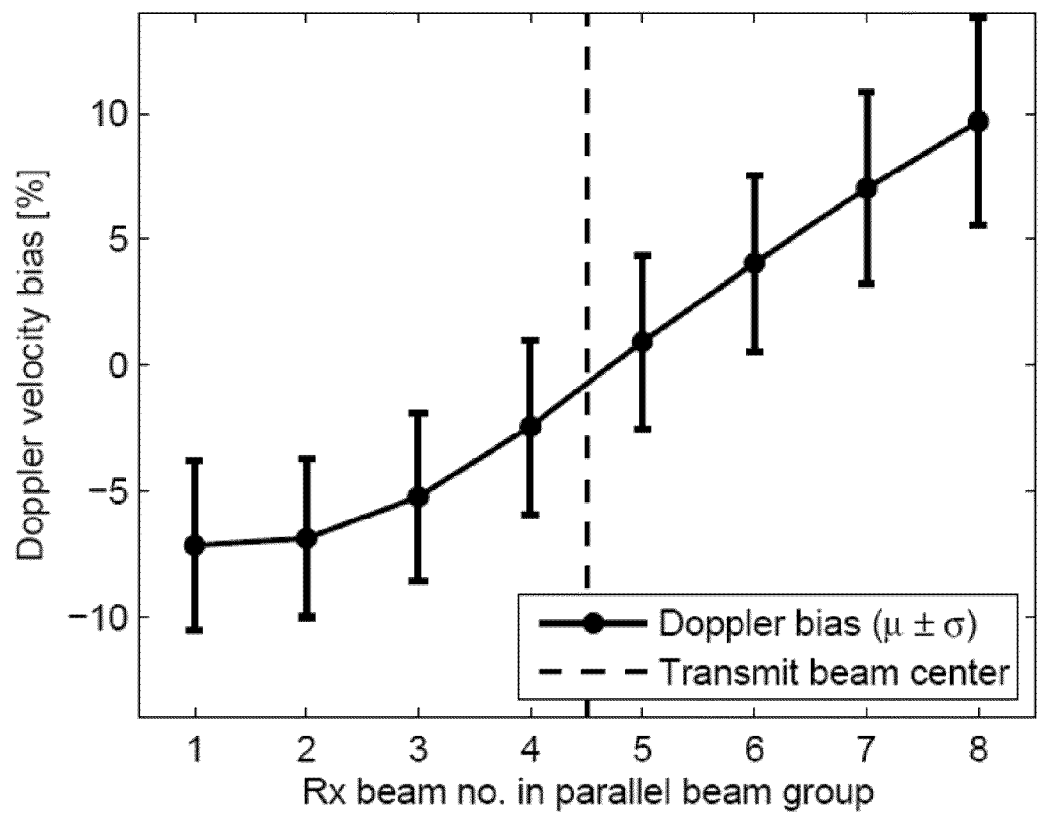
FIG. 11 simulated Doppler bias across parallel beams based on the information depicted in FIG. 8.

A computer simulation setup to emulate the in vivo imaging was conducted. The velocity estimates from one group of parallel beams is shown in FIG. 11 with mean and standard deviation from 20 realizations of the simulation. The results were averaged over the central 1.1 cm of the artery. Notice that the maximum Doppler bias is present for the outermost beams. The average curvature between 15 and 19 mm depth was found from simulations to be 3.6 degrees. The Doppler bias at beam 8 is 9.7±4.2%. Assuming a flat receive-beam, the pulse-echo curvature $\theta_b$ is 3.6 degrees/2. The in vivo angle $\theta$ between the beams and the flow is estimated to be 16 degrees, which should give an average Doppler bias of 10.9% for the outermost receive beam from 15 to 19 mm depth.

From the carotid images of FIG. 8 it is clear that the application of STB reduces the artifacts from traditional parallel beam processing. The reduction of artifacts can be seen both from visual inspection of the images, and from the cross correlation plots beneath each figure. In regular parallel beamforming the cross correlation drops markedly across parallel beam groups, with black bars, but this is restored for both STB methods. The two STB methods differ noticeably at the transitions between interleave groups, where the cross correlation of coherent STB drops while incoherent STB does not.

Another notable difference is in the power images of FIG. 8, where the signal at the interleave group transition in the center nearly disappears due to destructive interference. The power signal is used in some 2D color maps for vascular and cardiac imaging, so it is important that the power signal is also free from artifacts and dropouts.

The Doppler bias through the center of the artery is shown in FIG. 9, and the abrupt discontinuities are visible for regular parallel receive beams. Both STB methods remove the discontinuities across parallel beam groups, but incoherent STB performs better across interleave groups. This is further seen in FIG. 10, where only the bias at parallel beam group transitions is shown over the full width of the image to include all four interleave groups. For the depths 15-19 mm, around the maximum curvature seen in FIG. 3, the average change is 19.9% for regular parallel beam processing. This corresponds well with the simulated values shown in FIG. 11, which estimates the Doppler bias to be 9.7% for the edge beams, causing a total change of 2×9.7%=19.4%. Even the simple geometrical model with spherical wavefronts estimates the Doppler bias to be 2×10.9%=21.8% which corresponds reasonably well with the simulated and in vivo results.

For both STB methods the in vivo Doppler bias drops to approximately 3%, which is not that easily visible in the images. Coherent STB peaks in the error plot at two of the interleave group crossings, and dips at the third. This is due to the long time delay across interleave group crossing, which increases the variance of the estimates. This is not the case for incoherent STB.

Another effect to notice from FIG. 10 is how the Doppler bias gets smaller for increasing depths of the artery. This is because the transmit focus of the recording is at the bottom of the color flow region of interest, and close to the focal point the wavefronts are not expected to be curved, as shown in FIG. 3.

Figure 12:
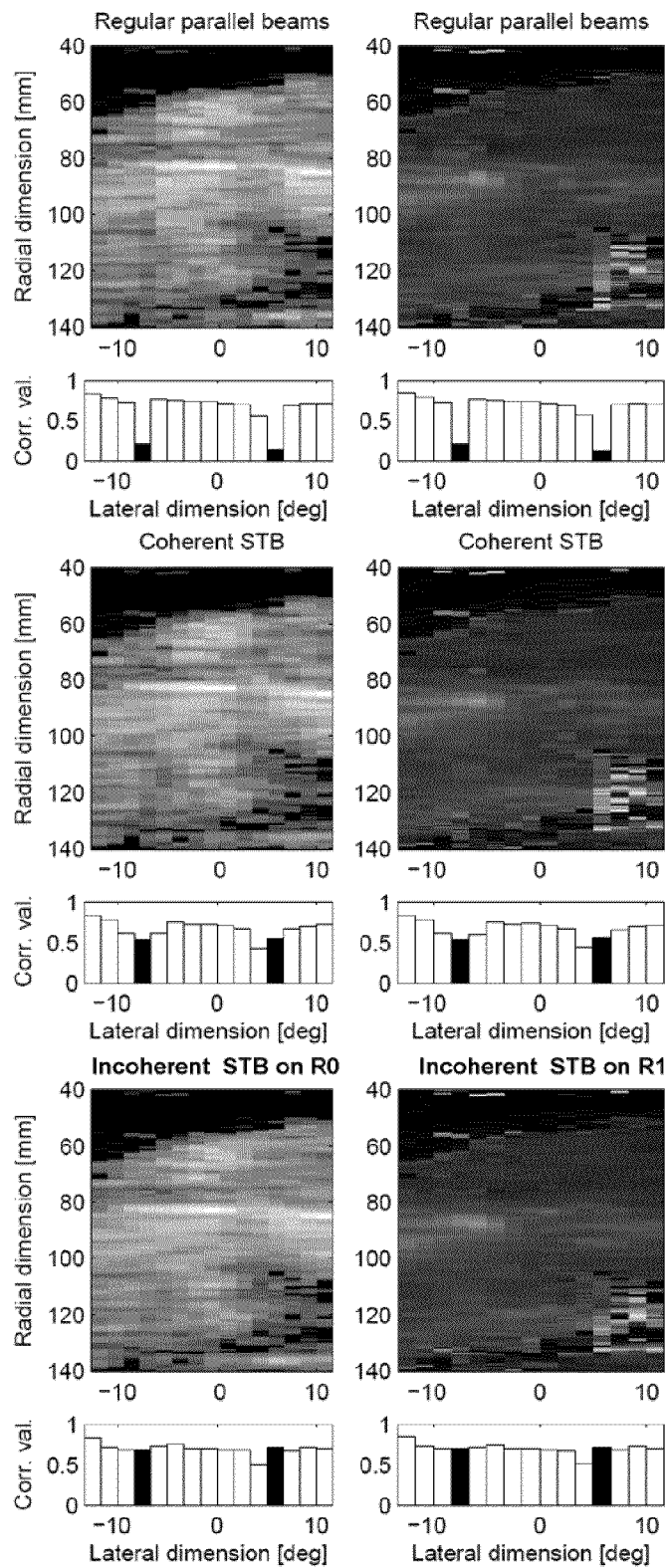
FIG. 12 illustrates power and velocity estimates of in vivo color flow images created using phased array imaging in accordance with embodiments of the present technology.

In connection with the phased array imaging, an M5S phased array probe (GE Vingmed Ultrasound) was used to image the left ventricle of a healthy volunteer. The resulting power and velocity images from the three parallel beam methods are shown in FIG. 12. The top pane shows standard parallel beam processing, the middle pane shows coherent STB, and the bottom pane shows incoherent STB. The images on the left side of FIG. 12 depict power estimates and the images on the right side of FIG. 12 depict velocity estimates. The cross correlation is shown below each image in the same way as for the linear images depicted in FIG. 8. Image acquisition settings can be found in Table I above. The images are not scan converted to make it easier to align the beams with the cross correlation plots. There are no interleave groups in these images, and the hemodynamics are changing rapidly. Note the artifacts at the transitions between groups of parallel beams.

The cardiac images of FIG. 12 indicate results similar to those discussed above in connection with FIG. 8. Both coherent and incoherent STB are able to reconstruct the beam-to-beam cross correlation, with incoherent STB showing better results.

To keep increasing the frame rate the number of parallel beams must increase, which in turn requires that the transmitted pulse must be wider. This is typically done by limiting the aperture, which reduces penetration and signal to noise ratio. At a certain point it is no longer beneficial to reduce the transmit aperture further, and it might be a better approach to use plane wave excitation, at least for linear array imaging where the diffraction focus of the unfocused aperture is typically below the region of interest.

In 3-D color flow imaging (3-D CFI) the trade-off between volume rates and image quality is particularly strained. For 3-D applications, and even more for 3-D CFI, parallel beamforming is particularly important to increase the volume rate without destroying the image quality. For 3-D imaging the beams are scanned two dimensionally, meaning that it is impossible to acquire overlapping beams, as required by STB, without a severe time penalty in at least one of the scanning dimensions. This makes 3-D CFI a good candidate for incoherent STB. It is still likely that the hemodynamics have changed significantly with the long data acquisition time of 3-D CFI, which makes it impossible to reconstruct the true velocity field. In this case incoherent STB will instead work as a temporal smoothing filter.

Parallel beam artifacts in color flow imaging are largely caused by the varying Doppler shifts recorded off center from a curved transmit beam. These artifacts can be reduced significantly by using synthetic transmit beams (STB). With a small time delay between overlapping beams coherent STB works well. With longer time delays, for instance across interleave groups, it is better to perform incoherent STB on the auto-correlation estimates instead of coherently on RF/IQ data. STB reduces the need for lateral smoothing of color flow images made with several parallel beams, meaning that color flow images with a higher resolution can be obtained with a higher frame rate than can be obtained without STB.

Figure 13:
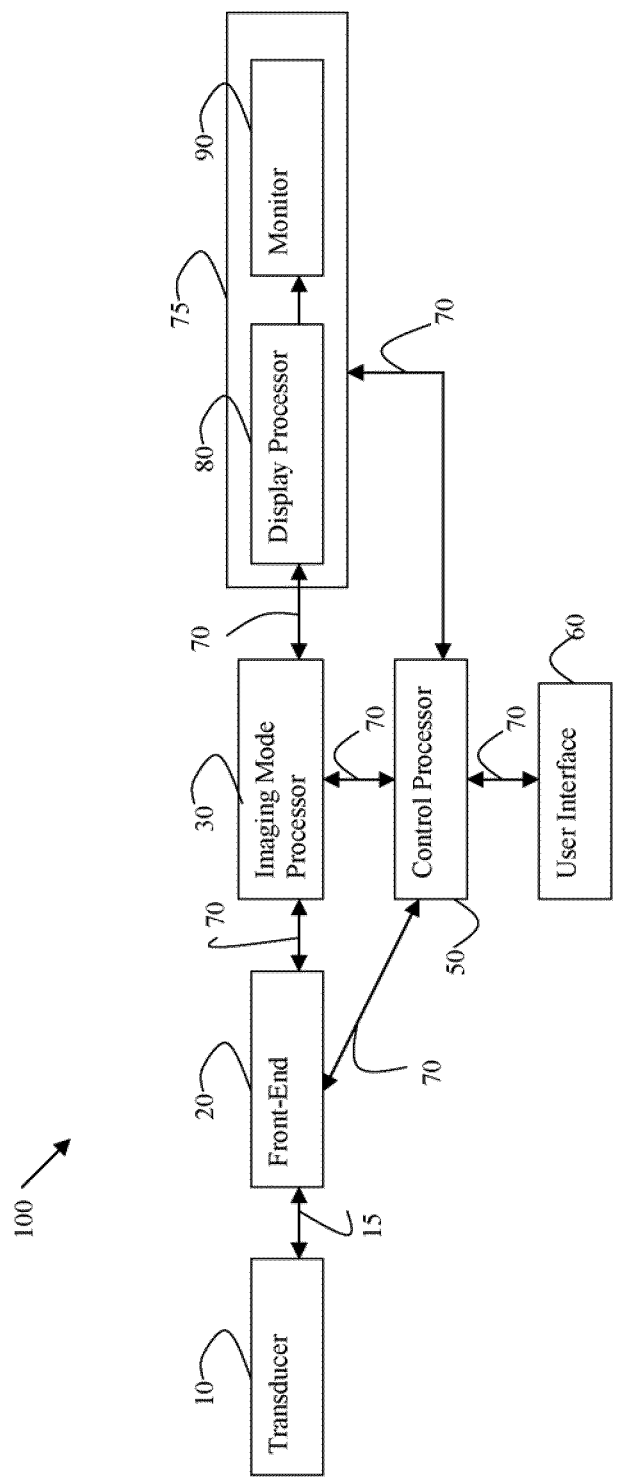
FIG. 13 illustrates a block diagram of an ultrasound imaging system used in accordance with an embodiment of the present technology.

FIG. 13 illustrates a block diagram of an ultrasound imaging system 100 used in accordance with an embodiment of the present technology. The system 100 includes a transducer 10, a front-end 20, an imaging mode processor 30, a user interface 60, a control processor 50, and a display 75. In certain embodiments, the imaging mode processor 30 and the control processor 50 may be part of a back-end system.

The transducer 10 and front-end 20 can be used together to create a beam pattern that is used to create an image. The transducer 10 can be used to transmit ultrasound waves into a subject by converting electrical analog signals to ultrasonic energy. The transducer 10 can also be used to detect ultrasound waves that are backscattered from the subject by converting ultrasonic energy to analog electrical signals. In certain embodiments, the transducer 10 can be a linear array or a phased array. The front-end 20 can include a receiver, a transmitter and/or a beamformer. The front-end 20 can be used to create transmitted waveforms, beam patterns, receiver filtering techniques, and demodulation schemes that can be used for various imaging modes. The front-end 20 can interface with the transducer 10 via an analog interface 15. The front-end 20 can interface with the imaging mode processor 30 and the control processor 50 via a digital bus 70. The digital bus 70 can include several digital sub-buses. The digital sub-buses can have separate configurations and provide digital data interfaces to various parts of the ultrasound imaging system 100.

Once a beam pattern has been focused, the beam pattern can be output from the front-end 20 to the imaging mode processor 30 in the form of digital signal data. The imaging mode processor 30 can process the received digital signal data to produce estimated parameter values. The imaging mode processor 30 can pass the estimated parameter values to a control processor 50 over the digital bus 70. The imaging mode processor 30 can also pass the estimated parameter values to the display 75 via the digital bus 70.

The display 75 can include a display processor 80 and a monitor 90. The display processor 80 can accept digital parameter values from the imaging mode processor 30 and the control processor 50. The display processor 80 can perform scan-conversion functions, color mapping functions, and tissue/flow arbitration functions, for example. The display processor 80 can process map and format the digital data for display, convert the digital display data to analog display signals, and pass the analog display signals to the monitor 90. The monitor 90 can accept the analog display signals from the display processor 80 and display the resulting image. An operator may view the image on the monitor 90.

The control processor 50 is the central processor of the ultrasound imaging system 100. The control processor 50 can interface with other components of the ultrasound imaging system 100 using the digital bus 70. The control processor 50 can execute various data algorithms and functions for various imaging and diagnostic modes. Digital data and commands can be transmitted and received between the control processor 50 and other components of the ultrasound imaging system 100. In certain embodiments, control processor 50 can be configured to apply coherent STB and/or incoherent STB, as discussed above, using the received digital signal data. In certain embodiments, functions performed by the control processor 50 can be performed by multiple processors and/or can be integrated into the imaging mode processor 30 and/or the display processor 80. In another embodiment, the functions of the processors 30, 50, and 80 can be integrated into a single personal computer ("PC") backend.

The user interface 60 can allow user commands to be input by the operator to the ultrasound imaging system 100 through the control processor 50. The user interface 60 can include a keyboard, mouse, switches, knobs, buttons, track ball, and/or on screen menus, for example.

Figure 14:
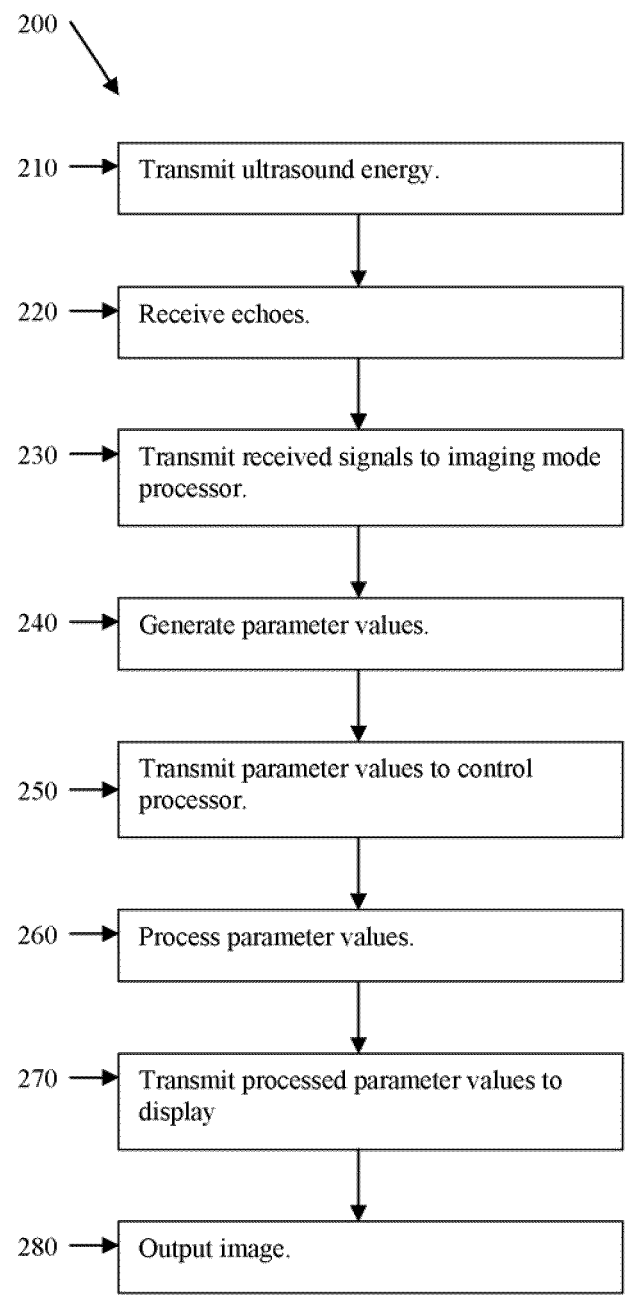
FIG. 14 illustrates a method for ultrasound imaging used in accordance with an embodiment of the present technology.

FIG. 14 illustrates a method 200 for ultrasound imaging used in accordance with an embodiment of the present technology. At 210, ultrasound energy is transmitted. For example, in certain embodiments, a transducer transmits ultrasound energy into a subject, such as a patient. For example, in certain embodiments, the ultrasound energy that is transmitted by the transducer can be transmitted in accordance with the transmission schemes depicted in FIGS. 5, 7B and/or 7C. Those skilled in the art will appreciate that other transmission schemes can be used when applying aspects of the present technology.

At 220, ultrasound energy or echoes backscattered from the subject are received. For example, in certain embodiments, ultrasound energy or echoes backscattered from the subject are detected by a transducer and signals are received at a front-end in response to ultrasound waves backscattered from the subject. For example, in certain embodiments, the ultrasound energy that is received can be received in accordance with any of the receive schemes depicted in FIGS. 5, 7B and/or 7C. Those skilled in the art will appreciate that other receive schemes can be used when applying aspects of the present technology.

At 230, the received signals are transmitted to an imaging mode processor. For example, in certain embodiments, the received signals are transmitted from a front-end to an imaging mode processor using a digital bus.

At 240, parameter values are generated. For example, in certain embodiments, an imaging mode processor generates parameter values based on the received signals.

At 250, the parameter values are sent to a control processor. For example, in certain embodiments, the parameter values are transmitted from an imaging mode processor to a control processor using a digital bus.

At 260, parameter values are processed. For example, in certain embodiments, a control processor processes the parameter values for use in display, storage and diagnostics at a display. In certain embodiments, the control processor processes the image data parameter values to reduce artifacts and process resulting image(s), for example. In certain embodiments, the control processor can be configured to apply coherent STB and/or incoherent STB, as discussed above, using the received signals.

At 270, processed parameter values are transmitted. For example, in certain embodiments, processed parameter values are transmitted to a display. In certain embodiments, a display processor can also process parameter values from a plurality of focal zone images to produce a combined image in conjunction with and/or in addition to the control processor, for example.

At 280, an image is output. For example, in certain embodiments, a diagnostic image is produced and output at a monitor. In certain embodiments, the image may be stored, displayed, printed and/or further transmitted, for example. In certain embodiments, the display processor can produce the diagnostic image using the processed parameter values from the digital signal data.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

One or more of the steps of the method 200 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. For example, certain embodiments provide a computer-readable storage medium encoded with a set of instructions for execution on a processing device and associated processing logic, wherein the set of instructions includes a routine(s) configured to provide the functions described in connection with the method 200 described in connection with FIG. 13.

Applying the method 200 as described above, and/or in light of the embodiments described herein, for example, as described in connection with FIGS. 5, 7B, 7C and/or 13, can provide for reduction of multiline artifacts in Doppler imaging, thereby providing improved image quality.

Also, the ultrasound data acquired, analyzed and displayed in connection with Doppler imaging represents blood flow through arteries. In other words, outputting a visual display based on such data comprises a transformation of underlying subject matter (such as an article or materials) to a different state.

While the invention has been described with reference to embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for multiline ultrasound imaging comprising:
    transmitting, using at least one transducer, a first ensemble of ultrasound beams at a first spatial position, wherein transmission of each beam in the first ensemble results in a plurality of parallel receive beams that are located between the first spatial position and a second spatial position;
    transmitting, using the at least one transducer, a second ensemble of ultrasound beams at the second spatial position, wherein transmission of each beam in the second ensemble results in a plurality of parallel receive beams that are located between the first spatial position and the second spatial position;
    calculating, using at least one processing device, a first auto-correlation estimate based on at least two receive beams from said first ensemble of beams;
    calculating, using the at least one processing device, a second auto-correlation estimate based on at least two receive beams from said second ensemble of beams; and
    combining, using the at least one processing device, the first auto-correlation estimate and the second auto-correlation estimate.

2. The method of claim 1, wherein the combined auto-correlation estimates are used to make an image.

3. The method of claim 1, wherein each receive beam used to calculate the first auto-correlation estimate and the second auto-correlation estimate overlap spatially.

4. The method of claim 1, wherein each receive beam used to calculate the first auto-correlation estimate and the second auto-correlation estimate completely overlap spatially.

5. The method of claim 1, wherein half of the parallel receive beams that result from transmission of the first ensemble are located between the first spatial position and the second spatial position, and half of the parallel receive beams that result from transmission of the second ensemble are located between the first spatial position and the second spatial position.

6. The method of claim 1, wherein all beams in the first ensemble are transmitted before any beams in the second ensemble are transmitted.

7. The method of claim 1, wherein combining the first auto-correlation estimate and the second auto-correlation estimate comprises applying a linear interpolation function that decreases the weight applied for receive beams that are spatially located further away from the transmit beam.

8. The method of claim 1, wherein the at least two receive beams from both the first ensemble of beams and the second ensemble of beams are located between the first spatial position and the second spatial position.

9. An ultrasound imaging system comprising:
    a transducer configured to transmit and receive ultrasound beams; and
    a control processor operably connected to the transducer, the control processor configured to process information received at the transducer,
    wherein the transducer is configured to transmit a first ensemble of ultrasound beams at a first spatial position, wherein transmission of each beam in the first ensemble results in a plurality of parallel receive beams that are located between the first spatial position and a second spatial position,
    wherein the transducer is configured to transmit a second ensemble of ultrasound beams at the second spatial position, wherein transmission of each beam in the second ensemble results in a plurality of parallel receive beams that are located between the first spatial position and the second spatial position,
    wherein the control processor is configured to a first auto-correlation estimate based on at least two receive beams from said first ensemble of beams,
    wherein the control processor is configured to calculate a second auto-correlation estimate based on at least two receive beams from said second ensemble of beams, and
    wherein the control processor is configured to combine the first auto-correlation estimate and the second auto-correlation estimate.

10. The system of claim 9, wherein the combined auto-correlation estimates are used to make an image.

11. The system of claim 9, wherein each receive beam used to calculate the first auto-correlation estimate and the second auto-correlation estimate overlap spatially.

12. The system of claim 9, wherein each receive beam used to calculate the first auto-correlation estimate and the second auto-correlation estimate completely overlap spatially.

13. The system of claim 9, wherein half of the parallel receive beams that result from transmission of the first ensemble are located between the first spatial position and the second spatial position, and half of the parallel receive beams that result from transmission of the second ensemble are located between the first spatial position and the second spatial position.

14. The system of claim 9, wherein all beams in the first ensemble are transmitted before any beams in the second ensemble are transmitted.

15. The system of claim 9, wherein combining the first auto-correlation estimate and the second auto-correlation estimate comprises applying a linear interpolation function that decreases the weight applied for receive beams that are spatially located further away from the transmit beam.

16. The system of claim 9, wherein the at least two receive beams from both the first ensemble of beams and the second ensemble of beams are located between the first spatial position and the second spatial position.

17. A non-transitory computer-readable storage medium encoded with a set of instructions for execution on a processing device and associated processing logic, wherein the set of instructions includes:
    a first routine that provides for controlling a transducer configured to transmit and receive ultrasound beams; and
    a second routine that provides for calculation of a plurality of auto-correlation estimates and combination of the auto-correlation estimates,
    wherein the first routine provides for transmission of a first ensemble of ultrasound beams at a first spatial position, wherein transmission of each beam in the first ensemble results in a plurality of parallel receive beams that are located between the first spatial position and a second spatial position, wherein the first routine provides for transmission of a second ensemble of ultrasound beams at the second spatial position, wherein transmission of each beam in the second ensemble results in a plurality of parallel receive beams that are located between the first spatial position and the second spatial position, wherein the second routine provides for calculation of a first auto-correlation estimate based on at least two receive beams from said first ensemble of beams, wherein the second routine provides for calculation of a second auto-correlation estimate based on at least one receive beam in the second plurality of parallel receive beams and at least one receive beam in the fourth plurality of parallel receive beams, and wherein the second routine provides for combining the first auto-correlation estimate and the second auto-correlation estimate.

18. The non-transitory computer-readable storage medium encoded with the set of instructions for execution on the processing device and the associated processing logic of claim 17, wherein the combined auto-correlation estimates are used to make an image.

19. The non-transitory computer-readable storage medium encoded with the set of instructions for execution on the processing device and the associated processing logic of claim 17, wherein each receive beam used to calculate the first auto-correlation estimate and the second auto-correlation estimate overlap spatially.

20. The non-transitory computer-readable storage medium encoded with the set of instructions for execution on the processing device and the associated processing logic of claim 17, wherein each receive beam used to calculate the first auto-correlation estimate and the second auto-correlation estimate completely overlap spatially.

21. The non-transitory computer-readable storage medium encoded with the set of instructions for execution on the processing device and the associated processing logic of claim 17, wherein half of the parallel receive beams that result from transmission of the first ensemble are located between the first spatial position and the second spatial position, and half of the parallel receive beams that result from transmission of the second ensemble are located between the first spatial position and the second spatial position.

22. The non-transitory computer-readable storage medium encoded with the set of instructions for execution on the processing device and the associated processing logic of claim 17, wherein all beams in the first ensemble are transmitted before any beams in the second ensemble are transmitted.

23. The non-transitory computer-readable storage medium encoded with the set of instructions for execution on the processing device and the associated processing logic of claim 17, wherein combining the first auto-correlation estimate and the second auto-correlation estimate comprises applying a linear interpolation function that decreases the weight applied for receive beams that are spatially located further away from the transmit beam.

24. The non-transitory computer-readable storage medium encoded with the set of instructions for execution on the processing device and the associated processing logic of claim 17, wherein the at least two receive beams from both the first ensemble of beams and the second ensemble of beams are located between the first spatial position and the second spatial position.

* * * * *